(12) United States Patent
Knight et al.

(10) Patent No.: US 9,713,482 B2
(45) Date of Patent: Jul. 25, 2017

(54) CANNULA

(71) Applicant: Surgical Synergy Limited, Carmarthenshire (GB)

(72) Inventors: Martin Knight, Tenterton (GB); Roger John, Llanelli (GB)

(73) Assignee: Surgical Synergy Limited, Carmarthenshire (GB)

( * ) Notice: Subject to any disclaimer, the term of this patent is extended or adjusted under 35 U.S.C. 154(b) by 82 days.

(21) Appl. No.: 14/386,557

(22) PCT Filed: Mar. 21, 2013

(86) PCT No.: PCT/GB2013/050734
§ 371 (c)(1),
(2) Date: Sep. 19, 2014

(87) PCT Pub. No.: WO2013/140172
PCT Pub. Date: Sep. 26, 2013

(65) Prior Publication Data
US 2015/0065794 A1    Mar. 5, 2015

(30) Foreign Application Priority Data
Mar. 21, 2012    (GB) .................................. 1204912.8

(51) Int. Cl.
*A61B 1/00* (2006.01)
*A61B 17/34* (2006.01)
(Continued)

(52) U.S. Cl.
CPC ...... *A61B 17/3423* (2013.01); *A61B 1/00087* (2013.01); *A61B 1/00154* (2013.01);
(Continued)

(58) Field of Classification Search
CPC .............. A61B 1/0008; A61B 1/00096; A61B 1/00098; A61B 1/00087; A61B 1/00091; A61B 1/00094
(Continued)

(56) References Cited

U.S. PATENT DOCUMENTS 5,224,954 A    7/1993  Watts et al.
5,957,937 A    9/1999  Yoon
(Continued)

FOREIGN PATENT DOCUMENTS

EP    1344497 A1    9/2003
EP    1985226 A2    10/2008
(Continued)

*Primary Examiner* — Timothy J Neal
(74) *Attorney, Agent, or Firm* — Dinsmore & Shohl LLP

(57) ABSTRACT

The present invention relates to an improved cannula that enables a plurality of applications to such as tools to be utilized through a single cannula. According to the present invention there is a cannula having a distal end for insertion into a body, the distal end defining an opening to a primary conduit extending along the longitudinal axis of the cannula. The cannula further comprises a tool element for providing a tool function at or adjacent the distal end of the cannula. At least a portion of the tool element is arranged to be moveable outwardly relative to the longitudinal axis of the cannula. Accordingly, it is beneficial that more than one function can be provided at the distal end of the cannula reducing the trauma to the patient and improving access for the surgeon.

14 Claims, 4 Drawing Sheets

(51) Int. Cl.
  *A61B 17/02* (2006.01)
  *A61B 1/05* (2006.01)
  *A61B 1/06* (2006.01)
  *A61B 1/04* (2006.01)
  *A61B 17/29* (2006.01)
  *A61B 90/30* (2016.01)
  *A61B 90/00* (2016.01)

(52) U.S. Cl.
  CPC .............. *A61B 1/05* (2013.01); *A61B 1/0676* (2013.01); *A61B 17/0218* (2013.01); *A61B 17/3417* (2013.01); *A61B 17/3421* (2013.01); *A61B 17/3431* (2013.01); *A61B 1/00098* (2013.01); *A61B 90/30* (2016.02); *A61B 90/361* (2016.02); *A61B 2017/0225* (2013.01); *A61B 2017/2906* (2013.01); *A61B 2017/346* (2013.01); *A61B 2017/3445* (2013.01); *A61B 2017/3447* (2013.01); *A61B 2017/3456* (2013.01)

(58) Field of Classification Search
  USPC .................. 600/104, 114, 153, 157, 204
  See application file for complete search history.

(56) References Cited

U.S. PATENT DOCUMENTS

| | | | |
|---|---|---|---|
| 2005/0085691 A1 | 4/2005 | Nakao | |
| 2005/0234294 A1* | 10/2005 | Saadat | A61B 1/0008 600/104 |
| 2009/0149716 A1* | 6/2009 | Diao | A61B 1/00085 600/202 |
| 2009/0318758 A1* | 12/2009 | Farr | A61B 1/0638 600/112 |
| 2011/0098529 A1* | 4/2011 | Ostrovsky | A61B 1/0008 600/104 |
| 2011/0118543 A1* | 5/2011 | Dosher | A61B 17/3421 600/104 |
| 2011/0166455 A1 | 7/2011 | Cully | |
| 2013/0102843 A1* | 4/2013 | Feuer | A61B 1/00087 600/109 |

FOREIGN PATENT DOCUMENTS

| | | |
|---|---|---|
| EP | 1992300 A2 | 11/2008 |
| WO | WO-0033909 A1 | 6/2000 |
| WO | WO-2005104927 A2 | 11/2005 |
| WO | WO-2010111629 A2 | 9/2010 |

* cited by examiner

CANNULA

CROSS-REFERENCE TO RELATED APPLICATIONS

This application is the U.S. National Phase of PCT/GB2013/050734, filed Mar. 21, 2013, which claims priority to GB 1204912.8, filed Mar. 21, 2012, the contents of which are incorporated herein in its entirety.

The present invention relates to an improved cannula that enables a plurality of applications such as tools to be utilised through a single cannula.

In laparoscopy and keyhole surgery cannulas are well known as being a guide and a pathway to ensuring the repeatable positioning of secondary probes and also a passage for the surgical instrument.

The conventional practice in inserting a primary cannula is first to create an entry portal or minimal point of insertion in a strategic position that enables the surgeon to gain optimal access to the surgical target. This may allow access to a visceral cavity distended by the insertion of a gas to separate the body wall(s) from the viscera or where more extensive tissues are to be traversed, a fine guide wire or trace immediately adjacent the point where the procedure will take place will be inserted under X-Ray or CT/MRI or other scanning means. The primary cannula is then passed through the gas retaining portal for visceral surgery or follows the wire to the position of the surgical target and is finally guided into place by X-Ray or other non-invasive location methods. Once the primary cannula is secured in place the various instruments would enter the primary cannula through a series of gate valves and are positioned near the surgical target and deployed to effect surgical procedure. Initially these will be an endoscope (telescope) with illumination at the tip and a method of irrigation with a suction head to extract and remove unwanted fluids and surgical debris. The next stage would be to enter into the primary cannula the appropriate surgical instrument with which to perform the procedure.

A disadvantage embodied within the present design of cannulas is their ability to accept a plurality of probes due to the limitation of space within the stem. A solution is to use a cannula with a greater cross section or better optimise the available space within the outside diameter (OD) to accommodate the multiplicity of probes. However, this is not easy and the principal problem would be the unacceptable growth in diameter in both making the device unwieldy and difficult to accurately position where there is limited space available and access is difficult. An alternative consideration is to use multiple, primary cannulas to accommodate the necessary probes and surgical instruments. This again has significant associated problems as the amount of trauma caused to the associated tissue(s) adjacent to where the primary cannulas have entered may even be greater than that of a conventional surgical wound and any advantage offered by minimally invasive surgery would be negated. This is even though there has been recent availability of micro miniature cameras and high intensity LED lighting. Cameras that include a lens system which are now available that have a diameter of less than 1.8 mm and an overall body length of 5 mm, and the camera has now reached a size where the supporting structure may for stability purposes will be larger than the camera.

To overcome some of the issues highlighted and address further needs of the surgeon an improvement to the conventional primary access cannula is required.

According to the present invention there is a cannula having a distal end for insertion into a body, the distal end defining an opening to a primary conduit extending along the longitudinal axis of the cannula, the cannula further comprising a tool element for providing a tool function at or adjacent the distal end of the cannula, wherein at least a portion of the tool element is arranged to be moveable outwardly relative to the longitudinal axis of the cannula.

The present invention overcomes several problems relating to the multiplicity of probes and services required at the 'surgical bed/zone'. Typically, a variety of functions are required at the distal end of the cannula. The surgical instrument determined by the operation to be carried out is clearly critical, and then the additional functions such as a camera, light, or a suction tube outlet are also often required for ease of operation by the surgeon.

Outward movement of at least a portion of the tool element is beneficial as this increases the cross sectional area of the cannula. This beneficially increases the cross sectional area of the primary conduit and beneficially effectively pushes open the tissue surrounding the cannula.

The tool element preferably is moveable outwardly between a first configuration wherein at last part of the tool element at least partially occludes the primary conduit, and a second (laterally shifted) configuration wherein at least part of the tool element is withdrawn from the primary conduit. This opening in the laterally shifted configuration is the primary conduit for access by a surgical instrument.

The present invention has significant benefits over the prior art. The present invention enables access through a primary conduit for a surgical instrument whilst there is also provided a tool element and even more beneficially a plurality of tool elements. The tool elements preferably form an array about the primary conduit. The at least one tool element is arranged to be moveable laterally relative to the longitudinal axis of the cannula. The tool element is therefore effectively splayed meaning that access through the primary conduit by the surgical instrument is ensured.

A function of a tool element is to provide some additional function for the surgeon during or in preparation for an operation. Accordingly, the tool element may simply comprise a conduit through which unwanted fluids and surgical debris can be removed. Alternatively, the tool element may include therein a light source such as an LED light source or may alternatively include therein a camera. A further tool element may be provided for example to provide irrigation or the input of specialist gases or fluid. Depending on the patient and the surgery the number and function of the tool elements can be adapted, or alternatively extra tool elements can be included however they may not all be required for that particular surgical procedure.

The tool element is preferably positioned at or adjacent the distal end of the cannula. It is important that positioning of the tool element is appropriate for its function. For example a tool element which accommodates a camera must be positioned at or adjacent the distal end of the cannula to ensure that the surgeon can visibly see the action of the surgical instrument.

In one embodiment a plurality of tool elements are provided which effectively extend beyond the end of the cannula and themselves form a new distal end of the cannula. The plurality of tool elements beneficially form a cluster about the primary conduit.

The tool element preferably comprises a receiving portion arranged to accommodate a tool. The receiving portion preferably is provided in a head. As described above a tool may for example be a camera or a light source or may simply be a conduit for introduction or extraction of a fluid or gas. In the event that a fluid or debris is to be extracted, a suction arrangement is provided at the proximal or surgeon control end of the cannula.

The tool element is preferably in communication with a tool conduit extending in the longitudinal length of the cannula. Even more beneficially the receiving portion is in communication with the tool conduit. In this manner for example debris may be moved from the operation site. Alternatively, the tool conduit may be arranged to supply power, to for example, an LED or camera.

The tool conduit beneficially extends inside the cannula. One or more tool conduits beneficially effectively form an outer wall of the primary conduit.

The receiving portion may preferably be a receiving conduit in communication with the tool conduit.

The tool element preferably comprises a tool finger. The tool finger has a longitudinal length preferably extending in the longitudinal axis of the cannula.

The tool finger is preferably secured to the cannula at the proximal end and the distal end is beneficially moveable relative to the proximal end. The distal end is beneficially not secured to the cannula. The tool finger may therefore comprise a leaf spring. The inner surface of the finger which will be described in more detail with reference to the accompanying drawings therefore may effectively form the wall defining the peripheral edge of the primary conduit.

The cannula preferably comprises a plurality of tool elements and preferably fingers. The plurality of tool fingers are preferably arranged at or adjacent the distal end of the cannula to define the opening to the primary conduit.

The receiving portion of the tool finger preferably comprises a head. At least the head of the tool finger is beneficially configured to be movable between a first configuration wherein at least a part of the head at least partially occludes the primary conduit, and a laterally shifted configuration wherein the head is (at least partially) withdrawn from the primary conduit. The head is beneficially provided at a distal end of the tool finger.

This provides a significant benefit as the outer dimensions of the cannula can be minimised for insertion into the patient and the outer dimension of the primary conduit can be reduced. Following insertion the head is shifted from the primary conduit outwardly relative to the longitudinal axis of the cannula thereby opening or increasing the cross sectional area of the primary conduit. Accordingly, the diameter of the primary conduit is beneficially effectively increased. This enables the introduction and removal of the appropriate surgical instrument.

The cannula further comprises an actuator arrangement for causing outward (radially) movement of the tool finger. The outward movement is beneficially in a splaying motion and the actuator is operable by the surgeon. The actuator arrangement preferably comprises a user operable actuator at or adjacent the proximal end of the cannula and an actuation element adjacent the tool finger. In use the surgeon moves the user operable actuator which is spaced apart from the actuation element causing or enabling the actuation element to splay apart the one or more tool fingers.

In one embodiment the tool fingers may be splayed by introduction of a surgical tool thus removing the requirement for an actuator.

The tool conduit preferably extends between the receiving portion and the proximal end of the cannula. The tool conduit is preferably flexible. The tool conduit beneficially has a cross sectional profile that changes as the cannula is deformed or bent. The tool conduit is therefore beneficially defined by a deformable material.

The tool finger is beneficially elastically deformable. It is beneficially secured at one end and beneficially operated in the form of a leaf spring.

Also according to the present invention there is a head for securing adjacent or to at an end of a cannula, the head defining a primary conduit there through, the head comprising a tool element for providing a tool function, wherein the tool element is arranged to be moveable outwardly relative to the longitudinal axis of the primary conduit of the head. Such a head may be secured to a cannula for use.

Embodiments of the present invention will now be described by way of example only with reference to the accompanying drawings in which.

Figure 1:
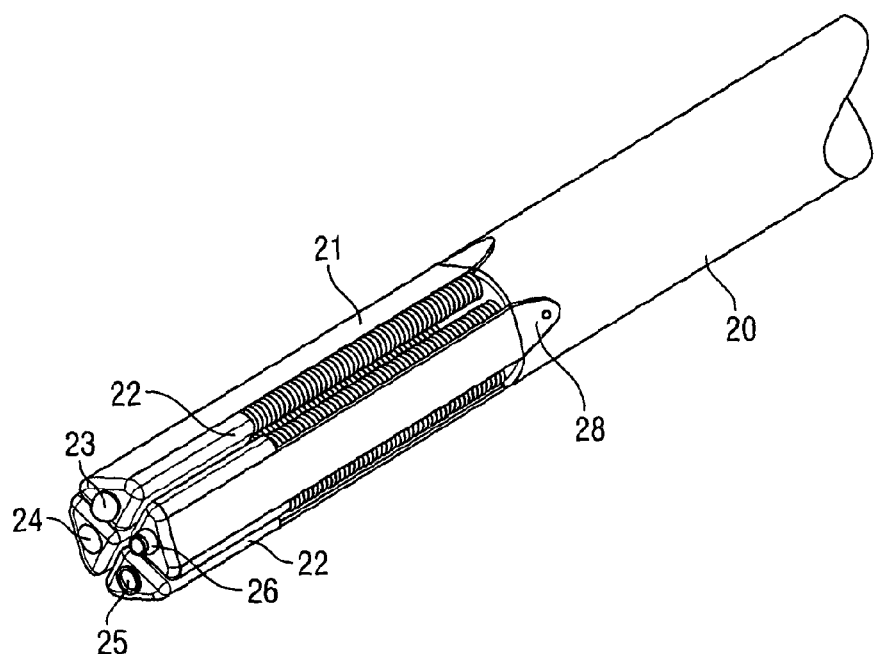
FIG. 1 is a schematic perspective view of the distal end of a cannula in a retracted configuration according to an exemplary embodiment of the present invention.

Referring to FIGS. 1 to 5 there is an exemplary embodiment that shows an arrangement that overcomes problems associated with a multiplicity of probes and services required at the distal or working end of the cannula. The exemplary embodiments incorporate within their design several of the functions that otherwise would have to be placed in an alternative cannula or would have to be placed down the primary cannula following extraction of a first probe.

The present arrangement comprises three major sections. The distal end or the working tip end that will enter the patient is shown in the Figures. This distal end of the cannula is positioned adjacent to the point of the surgical zone requiring the necessary procedures. The second section is the stem of the cannula that forms an integral part of the distal end. The proximal end of the cannula resides outside the patient and will form or include the handset that contains the various entry ducts and connections for the integral system as well as providing access for the associated surgical instruments.

The distal end of the cannula comprises one or more tool elements in the form of fingers 21 having a head or housing portion 22 arranged to contain the various functions. A variety of functions or tools may be provided as previously described such as a camera, a suction inlet and a conduit for receipt of debris, or a light source such as a LED as such example. In the exemplary embodiment there are provided four fingers 21 and various tools are provided at sites 23, 24, 25 and 26. The illumination may be in specific and multiple-frequency lighting. For some surgical procedures irrigation is also required. In other procedures specialist gases and fluids may be bought in to the sites 23, 24, 25 and 26. These sites may also provide a further conduit for any other clinical or surgical functions. The tool finger 21 is beneficially elongate in the longitudinal axis of the cannula 20 and the head 22 is movable outwardly and beneficially radially in relation to the longitudinal axis of the cannula 20. This may be achieved in various ways however in the exemplary embodiment each tool finger 21 is secured to the cannula 20 at fixing point 28. The tool finger 21 acts as a leaf spring and effectively is arranged to deflect about the fixing point 28. This is beneficial as the tool finger 21 is enabled to deflect elastically. This provides the benefit that once a force is removed a tool finger 21 returns to its original "at rest" configuration improving ease of insertion of the cannula 20 due to the effective constant outer diameter in the retracted configuration. This also works in reverse meaning that when the cannula 20 is ready for removal from the patient the tool finger returns to the original "at rest" configuration for ease of removal and reduction in impact to the surrounding tissue.

The head 22 is enlarged relative to the remaining portion of the tool finger 21. This configuration enables accommodation of the particular tool. It will be appreciated that in the event that the tool simply comprises a conduit then the required space is not as large as if, for example, the tool is an LED light. However, such a configuration is beneficial in that the distal end of the cannula 20 is therefore symmetrical meaning improved insertion characteristics. Furthermore, the opening of the conduit is ensured to be of a specified and predetermined cross sectional area.

It is beneficial that the tool finger 21 is riveted to the cannula 20 at fixing point 28 in order to provide a smooth outer surface for insertion and removal from a patient.

Figure 3:
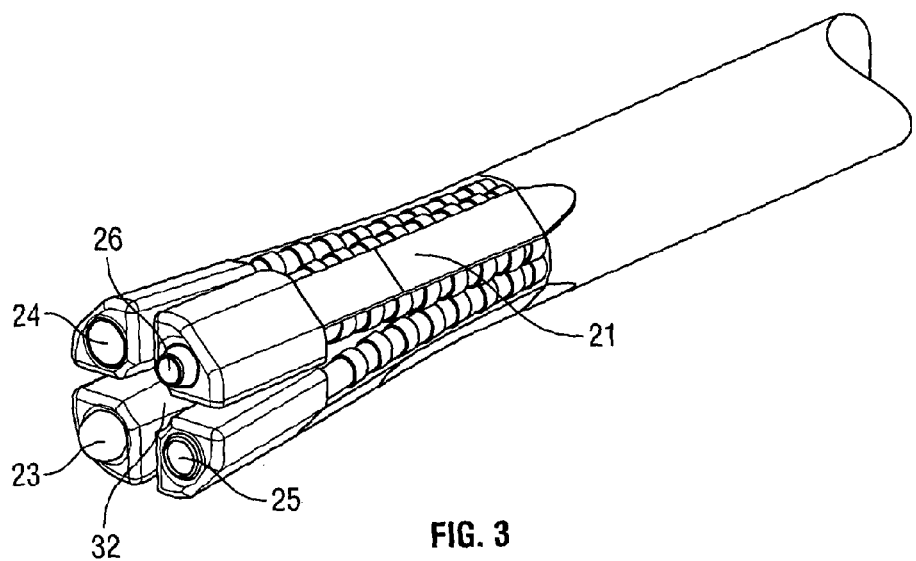
FIG. 3 is a schematic perspective view of the distal end of a cannula according to an exemplary embodiment of the present invention wherein the tool fingers are in an expanded or splayed configuration.

As will be seen in FIG. 1, in such a configuration wherein the tool fingers are in the contracted configuration there is no access for a surgical tool. FIG. 3 shows the tool fingers 21 in a splayed configuration. The tool fingers are configurable from a rest or contracted configuration to a splayed configuration. Splaying of the one or more tool fingers 21 may be achieved by a variety of options. A drive ring for example (not shown) which may be actuated from the proximal end of the cannula 20 by a surgeon may be provided which presents motion and force at a leading edge 30 of the head 22. The leading edge 30 is preferably provided by a radially inner surface of the tool finger 21. The leading edge 30 is beneficially tapered inwardly towards the opening of the cannula 20 meaning that in the contracted or rest configuration the effective opening at the tip of the cannula 20 is minimal. The drive ring may move axially pushing against the leading edge 30 causing the tool finger 21 to deflect about the fixing point 28.

Alternatively, deflection of the tool finger 21 may be achieved by the mechanical passage of a probe or tool which slides through the centre of the cluster of tool fingers 21 and accordingly causes the tool fingers to splay in a radial manner. The probe such as an endoscopic probe or surgical tool pushes against the leading edge 30 thereby splaying the tool fingers 21. It is envisaged that other arrangements for causing the tool fingers to splay may be provided.

Figure 2:
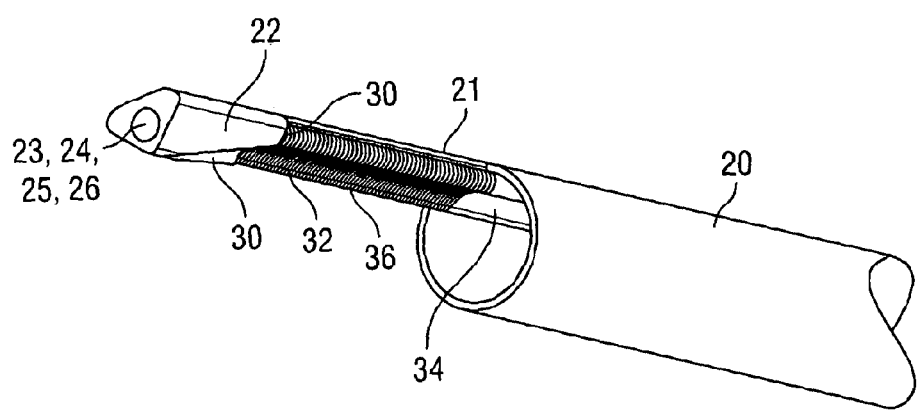
FIG. 2 is a schematic perspective view of the distal end of a cannula according to an exemplary embodiment of the present invention showing a single tool finger wherein representations of the remaining tool fingers have been removed for clarity purposes.

With reference in particular to FIG. 2, a tool finger 21 defines a conduit therethrough in communication with the head 22. Accordingly, the tool conduit 32 communicates either with the tool that may be provided in the head 22 or alternatively with the conduit or opening provided within the head. The tool conduit 32 projects in the longitudinal length of the tool finger 21. The tool conduit 32 then communicates with a secondary conduit 34 that extends through the longitudinal length of the cannula. Beneficially, the tool conduit 32 and the secondary conduit 34 are integrally formed with each other. The secondary conduit 34 nests adjacent the inside wall of the primary cannula 20. The secondary conduit 34 extends from the handset end of the primary cannula 20 and projects through the tool conduit 32 to the head 22 at the tip of the tool finger 21. Through this secondary cannula 34 services such as suction irrigation and electrical connections to the functions contained with the head 22 are provided.

As the tool finger 21 is arranged to splay or articulate, a proportional degree of motion must occur in the tool conduit 32. In one embodiment this degree of motion is achieved by placing a series of slots 36 (optionally helically) arranged to enable free motion that will not impinge upon the natural spring action of the tool finger 21. These slots 36 are also arranged to ensure a condition of motion to the tool finger 21 which will have a secondary effect to create an angle of presentation for the tool functions such as a direction of irrigation or the site of a camera. This motion created ensures a continuous secondary conduit and ensures a flexible nature of this conduit. The intervening gaps presented by the slots may be sealed with an elastomer that bridges the width of the cut and reinstates the hermetic nature of the secondary conduit. It is, however, envisaged that alternative means of providing flexibility to the tool conduit 32 may be achieved. It is also noted that the cross sectional area of the tool conduit 32 and secondary conduit 34 is shaped such that the inner surface that defines the conduit of the primary cannula is curved to define a primary conduit of generally round cross section.

Figure 4:
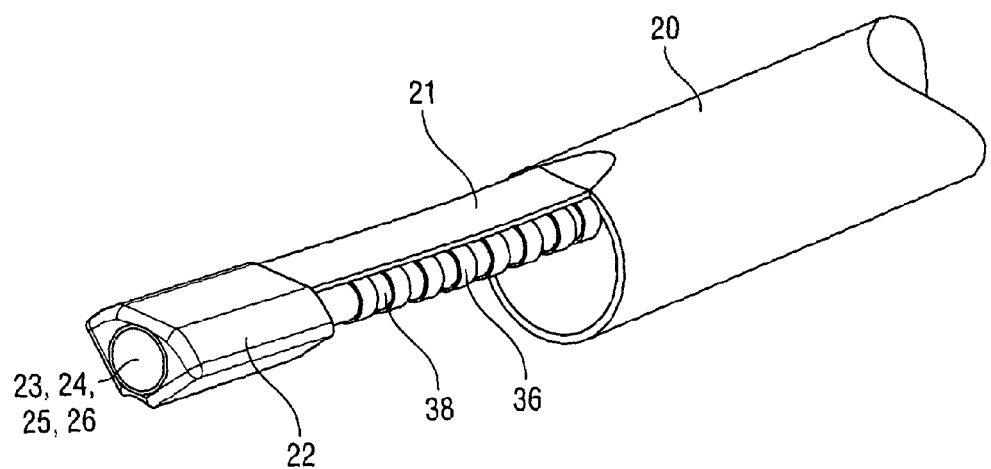
FIG. 4 is a schematic perspective view of the distal end of the cannula showing one tool finger for clarity purposes.
Figure 5:
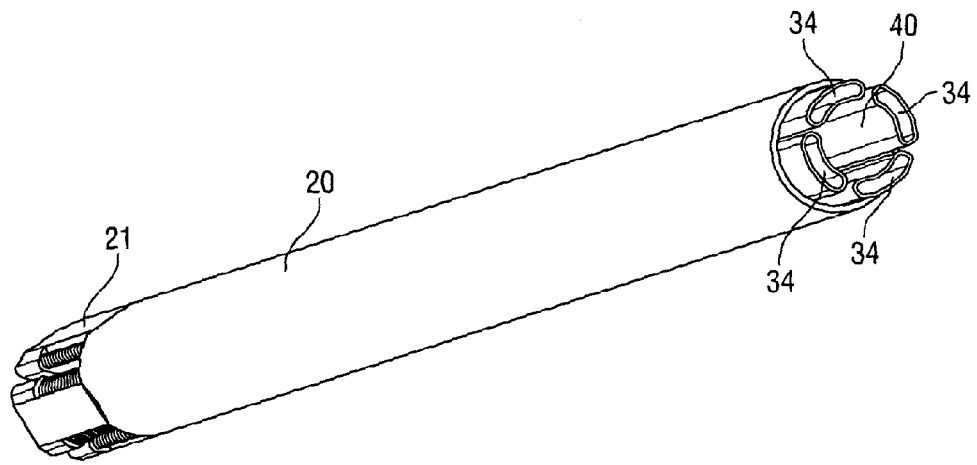
FIG. 5 is a schematic perspective view of the arrangement of the cannula showing therein the tool conduits extending in the longitudinal length of the cannula.

The slots 36 are better shown in FIG. 4 and clearly show an elastomer 38 therebetween. FIG. 5 more carefully illustrates the continuation of the primary conduit 40 and the secondary conduits 34 that nest adjacently in a surface of the cannula 20. The internal surface configuration of the secondary conduits 34 define an approximate cylindrical cross section of the primary conduit 40 enabling ease of passage of a surgical tool.

In use in one embodiment a force is applied to a drive ring which causes a radial element to slide along the leading edge 30 causing the tool fingers 21 to be driven laterally away from the central access of the cannula. In an alternative embodiment it is a surgical tool passed down the primary conduit 40 that acts on the leading edge 30 of each of the tool fingers 21 causing the lateral movement of the tool fingers. Either of these motions causes movement of the head 22 radially outwardly as a result of the tool finger 21 deflecting about the fixing point 28. The surgeon can then ensure accurate location of the surgical tool which has not been shown in the Figures through the primary conduit 40 which is beneficially assisted by at least one of the functions provided in a head 22 such as a camera and/or light. Each function is operable by the surgeon at the proximal end of the cannula 20 and one or more of the functions can be used at the same time meaning the surgeon has much improved access to the surgical area as waste material can easily be removed and a light and camera are ensured to be close to the area in which the surgical instrument is operated.

As indicated above, there are a number of ways of achieving the motion of splaying of the tool fingers 21. Each of the tool fingers is beneficially splayed to the same degree. In other words, the tool head 22 of each of the tool fingers 21 is laterally moved by the same amount. As indicated above, this can be achieved by a variety of alternative configurations such as, for example, a concentric sleeve extending to and over the tool fingers 21 such that when the concentric sleeve is withdrawn (slid back) the individual tool fingers 21 naturally splay as a result of residual spring tendency. To return to the non-splayed configuration, the surgical tool would be withdrawn from the distal end whereupon the concentric sleeve would slide forward and over the splayed tool fingers causing a return to a concentric profile. Such an action may include wiping by the concentric sleeve to remove any tissue that may have built up between the tool fingers 21 thus ensuring an unobstructed collapse and clean withdrawal.

In an alternative embodiment, a hydraulic force may be applied to each tool finger 21 which may be self-contained within each tool finger 21 and fed by a micro-bore capillary tube from an integral actuator at the handset end of the individual secondary conduit 34. In such an embodiment, each hydraulic element could be entirely self contained in a sealed system.

A further significant advantageous feature of the arrangement as described is that it may be dismantled into its key elements for cleaning and sterilisation. It enables removal and replacement of a tool head 22 or tool finger 21 as required.

Figure 6:
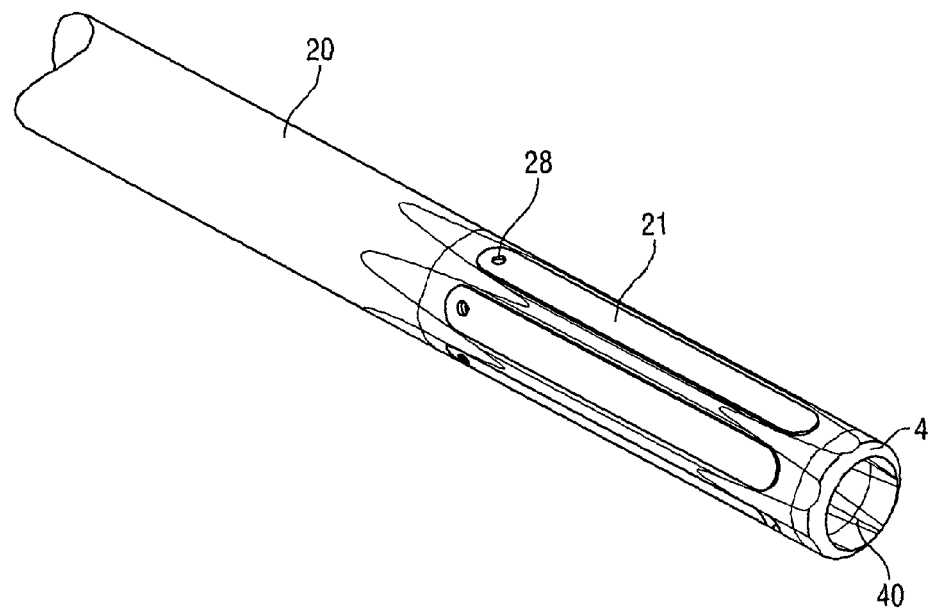
FIG. 6 is a schematic perspective view of the distal end of the cannula according to an alternative second exemplary embodiment of the present invention.
Figure 7:
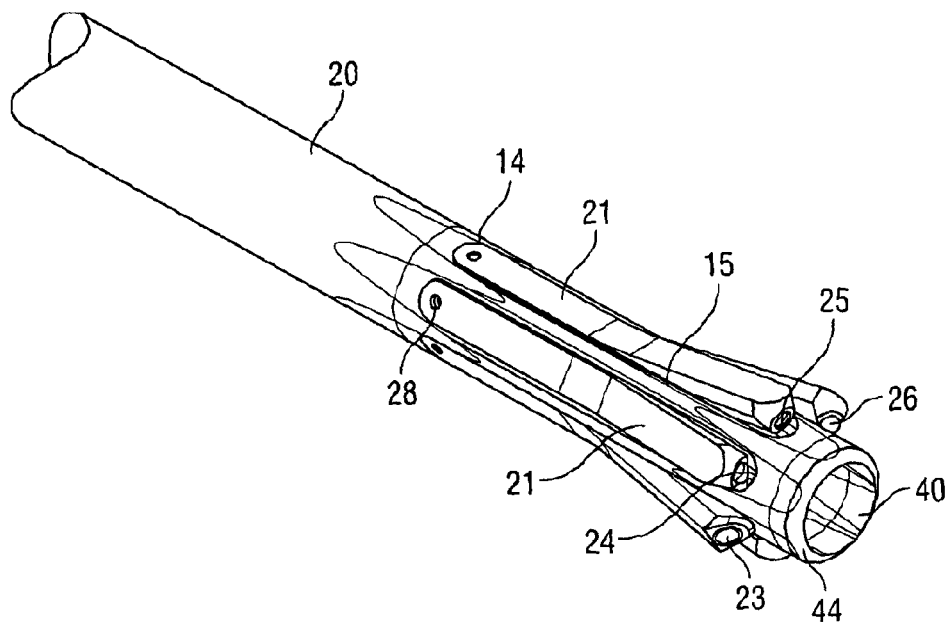
FIG. 7 is a schematic perspective view of the distal end of the cannula in the expanded configuration according a second exemplary embodiment of the present invention.
Figure 8:
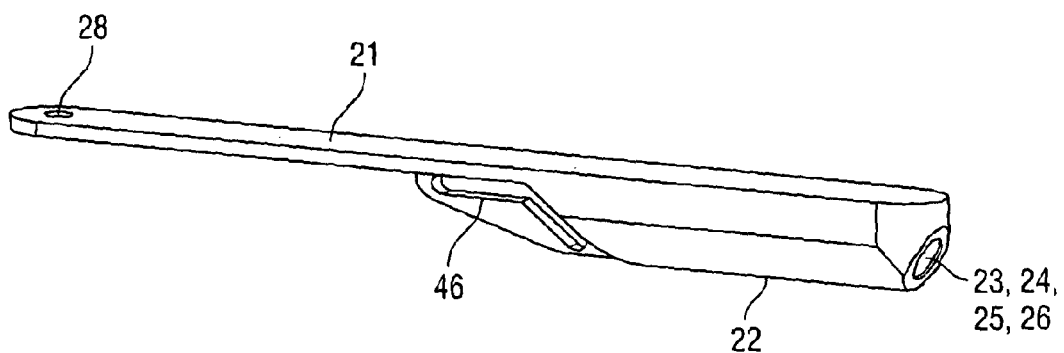
FIG. 8 is a schematic perspective view of a tool finger for use in a second exemplary embodiment of the present invention.

Referring to FIGS. 6 to 8, there is an alternative embodiment of the present invention wherein the tool fingers 21 seat within openings provided at the distal end of the cannula 20. The tool fingers are beneficially secured at fixing point 28 and project longitudinally relative to the cannula 20. A single tool finger is shown in FIG. 8. In such an embodiment the distal end 44 of the cannula 20 remains of a substantially constant diameter through which the surgical tool projects. The tool fingers 21 may be provided set back from the distal end 44 and a portion of the tool finger 21 is moveable between a contracted and expanded configuration where in expanded configuration, the tool sites 23, 24, 25 and 26 are accessible comprising a tool head 22 into which a tool is accommodated.

As shown in FIG. 8, a profiled section 46 is provided for receipt of a drive ring which causes a radial element to slide along the profiled section 46 provided on the underside of the tool finger 21 such that the tool fingers are driven laterally and away from the central access of the cannula 20. In doing so each tool finger 21 deflects thus driving the head 22 of the tool finger 21 outwardly thereby allowing unrestricted access for the surgical tool passing through the primary conduit 40.

Aspects of the present invention have been described by way of example only and it will be appreciated by the skilled addressee that modifications and variations may be made without departing from the scope of protection afforded by the appended claims.

The invention claimed is:

1. A cannula assembly comprising:
   a cannula having a proximal end and a distal end for insertion into a body, the distal end defining an opening to a primary conduit extending along a longitudinal axis of the cannula between the proximal end and the distal end of the cannula defining a tool pathway;
   a plurality of tool fingers positioned at or adjacent to the distal end of the cannula, each tool finger providing a tool function at or adjacent to the distal end of the cannula, each tool finger having a body adjacent to a proximal end of the tool finger and a head at a distal end of the tool finger for providing the tool function, the head being enlarged relative to the body of the tool finger, the head of at least one of the tool fingers having a camera provided therein, each tool finger being secured at the proximal end of the tool finger to the cannula;
   wherein each tool finger is elastically deformable outwardly relative to the longitudinal axis of the cannula and relative to the proximal end of the tool finger such that the head of the tool finger is operable to move between a first configuration where at least part of the head of the tool finger at least partially occludes the opening of the primary conduit and a laterally shifted configuration where the head of the tool finger at least partially moves laterally outwardly relative to the longitudinal axis of the cannula by elastically deforming the body of the tool finger; and
   wherein the primary conduit is defined by a plurality of tool conduits, each extending to a respective tool finger and being disposed circumferentially in the cannula.

2. A cannula assembly according to claim 1, wherein each head is a receiving conduit in communication with a respective tool conduit.

3. A cannula assembly according to claim 1, wherein the plurality of tool fingers are arranged at the distal end of the cannula to define the opening to the primary conduit.

4. A cannula assembly according to claim 1, further comprising an actuator arrangement for causing outward movement of each tool finger.

5. A cannula assembly according to claim 4, wherein the actuator arrangement comprises a user operable actuator at or adjacent the proximal end of the cannula, and an actuator element adjacent each tool finger.

6. A cannula assembly according to claim 1, wherein a light source is accommodated in one of the plurality of heads.

7. A cannula assembly according to claim 1, wherein the tool fingers are arranged to splay outwardly to the laterally shifted configuration.

8. A cannula assembly according to claim 1, wherein the plurality of tool fingers comprise four tool fingers.

9. A cannula assembly according to claim 1, wherein the tool fingers each project in a forward direction towards the head and wherein each head comprises a forwardly projecting pathway for the tool function.

10. A cannula assembly according to claim 1, wherein the tool fingers are deformable outwardly through action of a tool passing through the primary conduit and bearing on the tool fingers.

11. A cannula assembly according to claim 1, wherein each tool finger is biased to the first configuration.

12. A cannula assembly according to claim 1, further comprising a channel extending longitudinally in the cannula for carrying a power cable to the camera.

13. A cannula assembly according to claim 1, further comprising a secondary conduit extending longitudinally in the cannula for providing irrigation and/or a waste material exit pathway to the distal end of the cannula.

14. A cannula assembly comprising:
   a cannula having a proximal end and a distal end for insertion into a body, the distal end defining an opening to a primary conduit extending along a longitudinal axis of the cannula between the proximal end and the distal end of the cannula defining a tool pathway;
   a plurality of tool fingers positioned at or adjacent to the distal end of the cannula, each tool finger providing a tool function at or adjacent to the distal end of the cannula, each tool finger having a body adjacent to a proximal end of the tool finger and a head at a distal end of the tool finger for providing the tool function, the head being enlarged relative to the body of the tool finger, the head of at least one of the tool fingers having a camera provided therein, each tool finger being secured at the proximal end of the tool finger to the cannula; and a plurality of tool conduits, wherein the tool conduits nest adjacently in a surface of the cannula such that an internal surface configuration of the tool conduits defines an approximate cylindrical cross section of the primary conduit; wherein each tool finger is elastically deformable outwardly relative to the longitudinal axis of the cannula and relative to the proximal end of the tool finger such that the head of the tool finger is operable to move between a first configuration where at least part of the head of the tool finger at least partially occludes the opening of the primary conduit and a laterally shifted configuration where the head of the tool finger at least partially moves laterally outwardly relative to the longitudinal axis of the cannula by elastically deforming the body of the tool finger.

\* \* \* \* \*